United States Patent [19]

Ray et al.

[11] Patent Number: 4,907,605
[45] Date of Patent: Mar. 13, 1990

[54] ORAL TABACCO SUBSTITUTE

[75] Inventors: Jon P. Ray; Michael P. Ellis, both of San Antonio, Tex.

[73] Assignee: Advanced Tobacco Products, Inc., San Antonio, Tex.

[21] Appl. No.: 303,036

[22] Filed: Jan. 25, 1989

Related U.S. Application Data

[63] Continuation of Ser. No. 771,246, Aug. 30, 1985, abandoned, which is a continuation-in-part of Ser. No. 738,120, May 24, 1985, abandoned.

[51] Int. Cl.$^4$ ............................................. A24B 47/00
[52] U.S. Cl. ................................. 131;270; 131/273; 131/355
[58] Field of Search ................ 131/270, 335, 359, 369

[56] References Cited

U.S. PATENT DOCUMENTS

| | | |
|---|---|---|
| 2,860,638 | 11/1958 | Bartolomeo . |
| 3,200,819 | 8/1965 | Gilbert . |
| 3,422,819 | 1/1969 | Jones et al. ........................ 131/335 |
| 3,521,643 | 7/1970 | Toth . |
| 3,603,319 | 9/1971 | Badgett . |
| 3,757,798 | 9/1973 | Lambert . |
| 3,877,468 | 4/1975 | Lichtneckert et al. ............. 131/270 |
| 3,952,741 | 4/1976 | Baker . |
| 4,189,511 | 2/1980 | Levers et al. . |
| 4,284,089 | 8/1981 | Ray . |
| 4,635,651 | 1/1987 | Jacobs ................................ 131/329 |

*Primary Examiner*—V. Millin
*Attorney, Agent, or Firm*—Arnold, White & Durkee

[57] ABSTRACT

An oral nicotine dispenser comprising nicotine or a nicotine salt and a water-insoluble material capable of sorbing nicotine. The dispenser is able to slowly release the sorbed nicotine or nicotine salt in an oral environment. The water insoluble material may consist essentially of paper or a polymeric substance able to absorptively contain nicotine.

The water-insoluble material may be a substance such as paper or cellulose acetate. A water-insoluble polymeric substance such as a polyolefin, most preferably polyethylene or polypropylene may be used as the nicotine-holding material.

4 Claims, No Drawings

ORAL TOBACCO SUBSTITUTE

BACKGROUND OF THE INVENTION

This application is a continuation of Ser. No. 06/771,246 filed Aug. 30, 1985, now abandoned. Ser. No. 06/771,246 was a continuation-in-part of Ser. No. 06/738,120 filed May 24, 1985, now abandoned.

The present invention relates to a synthetic chewing tobacco comprising nicotine absorbed in a polymeric solid.

In recent years the usage of combusting tobacco has been suspected to be associated with numerous health hazards. Many of these health hazards are thought to result from carcinogenic materials produced by the tobacco combustion process itself.

As a result of such thinking, the use of tobacco in a non-combusting fashion has become more popular. Even more recently, the use of oral or "chewing" tobacco has been shown by some analysts to be associated with an increased risk of oral cancer. Oral or "chewing" tobacco comes in several forms such as leaf tobacco, snuff, plug and bags. Although tobacco has a high nicotine content, nicotine has not been found to be carcinogenic. Tobacco, however, also has a significant nitrosamine content and nitrosamines are known carcinogens.

Earlier studies have indicated that the reinforcing effects of any type of tobacco usage is due to the intake of nicotine. The various harmful or potentially harmful tobacco by-products appear to have little in the way of reinforcing physiological effects.

Non-tobacco forms of nicotine-yielding composites have been formulated. A nicotine-containing chewing gum has been produced for the specific purpose of aiding cigarette smokers during their period of withdrawal from cigarettes. With this gum, the nicotine is contained therein by interaction with an ion-exchange resin. Only vigorous chewing permits nicotine yield and, throughout passage in a canine digestive system, unchewed gum retained virtually all of its nicotine.

Nicotine-containing tablets comprising flavorings and inert materials have been created to permit a non-tobacco form of nicotine self administration. While nicotine-containing gums or tablets may provide doses of nicotine without harmful tobacco by-products, neither product may be readily consumed in a manner which a tobacco user familiarly associates with tobacco usage. For example, the gums require vigorous chewing and the tablets dissolve, neither chewing nor dissolving being involved in the usage of oral or "chewing" tobacco.

SUMMARY OF THE INVENTION

An oral nicotine dispenser comprising nicotine or a nicotine salt and a water-insoluble material capable of sorbing nicotine. The dispenser is able to slowly release the sorbed nicotine or nicotine salt in an oral environment. The water insoluble material may consist essentially of paper or a polymeric substance able to absorptively contain nicotine.

DESCRIPTION OF THE PREFERRED EMBODIMENTS

The oral nicotine dispenser of the present invention is a substitute for conventional chewing tobacco or dipping snuff. The oral nicotine dispenser of the present invention comprises a water-insoluble material with nicotine or nicotine salt sorbed into that material. By the term "sorbed" as used herein is meant absorption, adsorption or a combination thereof. By the term "water-insoluble" as used herein is meant qualitatively not dissolving to any substantial extent (e.g. less than 1%) in water at a pH between about 6.0 and 7.5 when immersed for extended periods of time (e.g. 24 hours).

The nicotine sorbed into the water-insoluble material is slowly released into an oral environment. By the term "slowly released" as used herein is meant released at a rate of less than 30% per hour. By the term "oral environment" as used herein is meant in an aqueous solution at a pH between about 6.4 and 7.0, at about 98.6° F. and with little or no stirring or agitation.

The water-insoluble material may, for example, be paper or cellulose derivatives such as cellulose acetate, although many other such substances well known to those skilled in the art may be used.

Nicotine salts to be sorbed into these materials are preferably first dissolved in a solvent such as ethyl alcohol. The nicotine salt solution is then applied to the material and the alcohol may be allowed to evaporate therefrom.

Nicotine may be of the d or the l configuration. Nicotine salts are preferably formed with nicotine and an organic acid such as citric acid, acetic acid, tartaric acid, lactic acid, oxalic acid, etc. Any organic acid which is biologically compatible, i.e., non-toxic at moderate levels, may be used to form preferred nicotine salts, although most preferably oxalic acid is used.

The nicotine itself, either used directly to form the oral nicotine dispensing device, or to make nicotine salts, may be obtained from Eastman Company as stock No. 1242, having a 98% nicotine content. This nicotine is most preferably further purified by a process such as vacuum distillation.

The oral nicotine dispenser of the present invention may also comprise a water-insoluble polymeric substance able to absorptively contain nicotine and slowly release the absorbed nicotine in an oral environment.

For the purpose of the present invention the water-insoluble polymeric substance should be biologically acceptable reversibly absorptive of nicotine, so that nicotine is absorbed and released. By the term "biologically acceptable" as used herein is meant having no toxic effects when held orally or accidentally swallowed. It is also important that the material be sufficiently absorbent of releaseable nicotine to hold enough nicotine so that at least about 1 microgram is dispensed in about one minute of immersion in an oral environment. The polymeric substance is typically a material generically described as an olefinic polymer. More specifically, the polymeric substance is preferably polyethylene or polypropylene but may also be any polyolefin or polyolefindiene such as polybutadiene, poly-1-butene, polyisobutylene, polyisoprene, poly-4-methyl pentene, or combinations thereof, for example.

Polymeric substances such as polystyrene and polycarbonate are dissolved by nicotine and thus not usable in the practice of the present invention. Polymers containing toxic or potentially toxic substances are not recommended for use.

Nicotine may be sorbed or similarly impregnated into the water-insoluble materials or polymeric substances of the present invention by a variety of means. For example, by immersion in liquid nicotine, by exposure to nicotine vapors or by impregnation with a nicotine-solvent mixture.

The water-insoluble materials or polymeric substances may by impregnated with nicotine prior to cutting or otherwise forming into suitable sizes and forms for oral use, or vice versa.

The preferable size and shape of the water-insoluble materials or polymeric substances is dependent on the intended mode of oral use. If a porous bag of suitable size to hold between a user's gums and cheek is to be used, the materials may be fibers or may be cut into numerous small strips. For example, a film having thickness of less than 1 mm might be cut into rectangular strips of about 3 mm by 10 mm. The porous bag may have heat-sealed edges. In other situations, where a porous bag is not used, the material or polymeric substance may be cut in an oval or rectangular shape, for example, of about 1 cm by 2 cm. Particularly where a water-insoluble material such as paper is used, it is contemplated that a nicotine-containing roll may be provided so that a user may detach a segment or plug of desired size for insertion between his gums and cheek, perhaps after brief mastication, if desired.

If desired, a pharmacologically acceptable anti-oxidant such as propyl gallate, butylated hydroxyanisole or butylated hydroxytolene may be added to impregnated nicotine to enhance its stability to air-induced oxidation.

Flavorants such as tobacco flavoring, menthol or methyl salicylate, for example, may also be added to impregnated nicotine to produce an oral nicotine dispenser with a desired pharmacologically acceptable flavor.

The following examples are presented to illustrate aspects and embodiments of the present invention and are not meant to limit the invention, unless specifically so stated in the claims.

EXAMPLE 1

Polyethylene Film Absorption from Liquid Nicotine

Two types of polyethylene film (1 mil thickness) from Phillips Petroleum, Bartlesville, OK were obtained: No. TR140, a blown film of high crystallinity; and No. OX611, a cast film of low crystallinity. Samples of both film types were weighed and immersed in nicotine (98% Eastman Kodak, Rochester, N.Y.) at 25° C. for 5 hours. After withdrawal from the nicotine, the film samples were carefully wiped until completely free of liquid, and weighed. The results of this immersion are shown in Table 1.

TABLE 1

Nicotine Absorption by Polyethylene Film

| Sample | Preliminary Weight | Postimmersion Weight | Nicotine Absorbed | % Nicotine (of original wt.) |
|---|---|---|---|---|
| TR140 | 84.9 mg | 86.8 mg | 1.9 mg | 2.2% |
| OX611 | 128.9 mg | 133.7 mg | 4.8 mg | 3.7% |

As the data in Table 1 indicates both types of polyethylene film absorb nicotine, the low crystallinity polyethylene absorbing nicotine more efficiently.

EXAMPLE 2

Absorption of Nicotine Vapor by Various Polymers

Valox (polybutyleneterphthalate) in various forms was obtained from General Electric (Polymer Products Department). Tedlar (polyvinylfluoride film) was obtained from DuPont de Nemours & Company. Gafphite 1600A (polybuteleneterephthalate) was obtained from General Aniline Fiber. PPH (Polypropylene homopolymer) was obtained from Teel Plastics, Baraboo, Wis. Various preweighed samples (from 40 mg to about 800 mg in weight) of these polymers were incubated in sealed containers with a nicotine saturated air for different times and at different temperatures and again weighed. The results of these manipulations are shown in Table 2.

TABLE 2

Percent Weight Gain For Various Polymers Subjected to Nicotine Vapors

| Sample | Temperature | Time (Days) | Weight Gain (wt. %) |
|---|---|---|---|
| Valox (10% glass filled) | ambient | 12 | 1.46 |
| Valox (10% glass filled) | 125° F. | 12 | 0.67 |
| Valox (40% glass filled) | ambient | 12 | 0.09 |
| Valox (40% glass filled) | 125° F. | 12 | 0.02 |
| Valox 310-083 | ambient | 7 | 0.08 |
| Valox 310-083 | 125° F. | 7 | 0.29 |
| Valox 310-095 | ambient | 7 | 0.10 |
| Valox 310-095 | 125° F. | 7 | 0.98 |
| Gafphite 1600A | ambient | 7 | 0.072 |
| Gafphite 1600A | 125° F. | 7 | 0.35 |
| Tedlar | ambient | 7 | 0.055 |
| Tedlar | 125° F. | 7 | 1.00 |
| PPH | 125° F. | 7 | 1.2 |
| PPH | 60° C. | 1 | 3.7 |
| PPH | 60° C. | 3 | 5.7 |
| PPH | 60° C. | 10 | 6.0 |
| PPH | 60° C. | 20 | 6.8 |
| PPH | 50° C. | 1 | 0.4 |
| PPH | 50° C. | 3 | 0.8 |
| PPH | 50° C. | 5 | 1.9 |
| PPH | 50° C. | 10 | 2.7 |
| PPH | 50° C. | 20 | 4.1 |
| PPH | 25° C. | 1 | 0.05 |
| PPH | 25° C. | 3 | 0.15 |
| PPH | 25° C. | 5 | 0.20 |
| PPH | 25° C. | 10 | 0.25 |
| PPH | 25° C. | 20 | 0.5 |
| PPH | 5° C. | 1 | 0.05 |
| PPH | 5° C. | 3 | 0.08 |
| PPH | 5° C. | 5 | 0.10 |
| PPH | 5° C. | 10 | 0.10 |
| PPH | 5° C. | 20 | 0.15 |

As the data in Table 2 indicates, under comparable conditions (polypropylene at 50° C. for 10 days and polybutylene terephthalate or polyvinylfluoride at 125° F. for 7 days), the polyolefin polypropylene is much more effective as a nicotine absorbent (2.7 wt. % gain) than is the polybutylene terephthalate (less than 1%) or polyvinyl fluoride (about 1%). Also, these results suggest the usability of such relatively nonabsorptive polymers for aspects related to the presently described oral nicotine dispenser where nicotine non-absorption is desirable such as the wrappings for storage.

EXAMPLE 3

Polyethylene Absorption of Vaporous Menthol

A low density polyethylene tube (8×84 mm) weighing 8.243 mg was sealed in a test tube with menthol crystals. The tet tube was then placed in an oven at 125° F. for 2 hr. The tube was removed from the test tube, washed with ethanol, dried and weighed. The tube then weighed 865.4 mg, showing a weight increase of 41.1 mg ascribable to absorbed menthol. This experiment indicates that menthol, as well as nicotine may be absorbed by polyethylene. Thus an oral nicotine dispenser comprising a polyolefin such as polyethylene may contain absorbed menthol as well as absorbed nicotine.

EXAMPLE 4

Polypropylene Absorption from Liquid Nicotine and Desorption Under Vacuum

Four polypropylene samples obtained from Teel, Baraboo, Wis., were washed, dried, weighed and immersed in liquid nicotine for 21 hours at 120° F. The samples were withdrawn, washed with water, dried and weighed again to determine the extent of nicotine absorption in the nicotine-loaded samples. These nicotine-loaded polypropylene samples were then placed in a vacuum dessicator, subjected to a vacuum of about 75 mm of pressure for 10 min. and reweighed to determine loss of absorbed nicotine. The results of these manipulations are shown in Table 3.

TABLE 3

| Polypropylene Absorption from Liquid Nicotine and Desorption Under Vacuum | | | | |
|---|---|---|---|---|
| | 1 | 2 | 3 | 4 |
| Sample weight (mg) | 428.5 | 429.3 | 511.0 | 623.4 |
| Sample weight after immersion | 443.8 | 455.6 | 540.5 | 640.7 |
| Nicotine absorbed (mg) | 15.3 | 31.7 | 29.5 | 17.3 |
| % nicotine of sample weight | 3.6 | 7.5 | 5.8 | 2.8 |
| Sample weight after 10 min. under vacuum | 443.4 | 454.5 | 539.9 | 640.6 |
| Mg nicotine desorbed under vacuum | 0.4 | 1.1 | 0.6 | 0.1 |

As the above data indicate, polypropylene is an effective nicotine absorbent and absorbed nicotine does not flash evaporate when subjected to a vacuum which would quickly evaporate free nicotine liquid. This observation indicates more than adsorption or superficial absorption, such as in surface crevices in the polyolefin.

EXAMPLE 5

Polypropylene Absorption from Liquid Nicotine, Time and Temperature Dependency Polypropylene homopolymer tubes (Teel Plastics) were weighed and immersed in liquid nicotine. After withdrawal, the tubes were washed, dried and weighed. Increases in weight were utilized to calculate wt % absorption. Table 4 shows data obtained from these manipulations.

TABLE 4

| Polypropylene Nicotine Absorption | | | | |
|---|---|---|---|---|
| | wt % absorption, at | | | |
| Time (hr) | 5° C. | 25° C. | 50° C. | 60° C. |
| 1 | 0.007 | 0.014 | 0.37 | 0.87 |
| 25 | 0.016 | 0.085 | 5.4 | 6.9 |
| 88 | 0.008 | 0.47 | 5.9 | 6.4 |
| 192 | 0.028 | 0.87 | 6.0 | 6.5 |

The data in Table 4 shows that polypropylene effectively absorbs liquid nicotine in a manner dependent on time and temperature. Hence polypropylene is demonstrated as a polyolefin useful as a polymeric substance of the present invention able to absorptively contain nicotine.

EXAMPLE 6

High Density Porous Polyethylene Absorption of Nicotine Vapors

Four samples (cylinders with about a ¼ inch diameter and 1½ inch length) of porous high density polyethylene were obtained from Porex Technologies (Fairburn, GA). These samples were weighed and then each incubated at ambient temperature in a sealed tube and in the presence of 40–50 mg nicotine. The weight of the samples were periodically determined and the resultant data shown in Table 6.

TABLE 5

| Nicotine Weight Gain of Porous High Density Polyethylene | | | | | |
|---|---|---|---|---|---|
| Original Sample No. | | 1 | 2 | 3 | 4 |
| Weight (mg) | | 689.3 | 692.0 | 699.3 | 694.3 |
| | | Increase in weight (mg) | | | |
| Incubation Temp. | | ambient | ambient | 120° F. | 120° F. |
| Incubation Time | 1 hr | 1.0 | 1.0 | 3.5 | 4.2 |
| | 2 hr | 1.5 | 1.7 | 3.6 | 5.9 |
| | 1 day | 6.2 | 6.1 | 12.9 | 13.6 |
| | 6 days | 11.3 | | 17.7 | |

The data in Table 5 demonstrates the nicotine-absorption ability of polyethylene when said polyethylene is in the physical form of a high density polyethylene porous plug.

EXAMPLE 7

Attempted Extraction with Ethanol of Absorbed Nicotine from a Porous Polyethylene Plug An aluminum tube with an interposed porous high density polyethylene plug (Porex Technologies) was constructed and the plug was loaded with 20 mg of liquid nicotine. A 35 cc volume of 95% ethanol was drawn through the loaded plug in a 3 second period and then analyzed for nicotine content. The volume of 95% ethanol, an excellent nicotine solvent under normal conditions, contained 1.4 mg of nicotine, this being about 7% of the absorbed nicotine. These data illustrate that rapid extraction of nicotine from a state of polyethylene absorption is not easily accomplished and that the nicotine had penetrated the polyethylene.

EXAMPLE 8

Attempted Extraction of Nicotine by 0.1M HCl from a Nicotine-Containing Polyethylene Tube A low density polyethylene tube (8×84 mm) weighing 743.5 mg and containing 22.3 mg of absorbed nicotine was immersed in 0.1M hydrochloric acid at ambient temperature for periods of 1 minute and 10 minutes. After washing, drying and weighing, the 1 min. HCl immersion was found to have caused a weight loss of 0.4 mg and the 10 min. immersion a weight loss of 1.4 mg. This experiment suggested that, should a nicotine containing polyethylene sample be ingested, that the internal emission of nicotine would be slow rather than immediate. It was also indicated that nicotine had deeply penetrated the polyethylene rather than being adsorbed or superficially absorbed.

This example demonstrates that, should an oral nicotine dispenser be swallowed and subjected to gastric acid, a large and immediate yield of nicotine will not occur.

EXAMPLE 9

Absorption of Nicotine Vapors by Several Materials at Different Temperatures Preweighed samples of various materials were sealed in tubes with excess nicotine vapors. After various periods of time at different temperatures, the samples were removed and reweighed. Increases in sample weight were calculated as weight percent (wt %) increases based upon the original sample weights.

Tip paper number MR-320 was obtained from the Schweitzer Paper Company, Division of Kimberly Clark, Neenah, Wis. Kimdura, a polypropylene trilaminate, was also obtained from Kimberly Clark. A polypropylene tube (PPT) was obtained from Teel Plastics, Baraboo, Wis. and polypropylene fiber (PPF) Type 701 from Hercules Plastics, Wilmington, Del. The absorption of nicotine by these samples, as shown in wt % increases is presented in Table 6. Tip paper provides an illustration of the nicotine-sorptive qualities of paper, which should be greatly accentuated with paper such as filter paper or blotting paper which have much greater surface to volume ratios.

TABLE 6

| Sample | Temp (°C.) | Absorption of Nicotine Vapor wt % nicotine | | | | |
|---|---|---|---|---|---|---|
| | | 1 day | 3 day | 5 day | 10 day | 20 day |
| Tip Paper | 5 | 1.8 | 2.5 | 1.9 | 3.6 | 2.7 |
| | 25 | 0.78 | 1.3 | 1.9 | 3.0 | 4.1 |
| | 20 | 4.0 | 7.4 | 7.5 | 6.4 | 13.0 |
| | 60 | 5.1 | 14.0 | 7.1 | 12.0 | 18.0 |
| Kimdura | 5 | 1.3 | 0.08 | 0.08 | 0.31 | 0.28 |
| | 25 | 0.11 | 0.16 | 0.33 | 0.30 | 0.58 |
| | 50 | 0.82 | 1.1 | 1.3 | 1.6 | 2.5 |
| | 60 | 1.3 | 3.0 | 3.5 | 4.2 | 6.2 |
| PPT | 5 | 0.03 | 0.07 | 0.08 | 0.11 | 0.14 |
| | 25 | 0.06 | 0.18 | 0.18 | 0.27 | 0.52 |
| | 50 | 0.40 | 0.74 | 1.9 | 2.7 | 4.1 |
| | 60 | 1.2 | 3.7 | 5.7 | 6.0 | 6.0 |
| PPF | 5 | 0.06 | 0.05 | 0.002 | 0.11 | 0.22 |
| | 25 | 0.07 | 0.12 | 0.24 | 0.15 | 0.64 |
| | 50 | 0.75 | 1.5 | 1.7 | 1.2 | 3.6 |
| | 60 | 1.6 | 3.2 | 5.1 | 2.9 | 8.7 |

As shown by the data in Table 6, tip paper, trilaminate polypropylene, polypropylene tube and polypropylene fiber all absorb nicotine vapors; and this absorption is proportional to time and temperature. Thus the suitability of these materials to contain nicotine in an oral nicotine dispenser is illustrated.

EXAMPLE 10

Nicotine Salt and Paper

A ⅜ inch by ¾ inch piece of Whatman #541 filter paper was immersed in an ethyl alcohol solution containing 5% nicotine salt. The nicotine salt was formed with tartaric acid. The filter paper was removed and the alcohol allowed to evaporate to produce an oral nicotine dispenser.

When an individual placed the oral nicotine dispenser between his cheek and teeth, the individual reported a prolonged sensation of nicotine-like stimulation, due to the slowly released nicotine salt.

EXAMPLE 11

Polyolefin Sheet or Plug

A ⅜ inch by ¾ inch piece of polyethylene sheet (5/1000 inch thickness) was soaked in nicotine at 100° F. for 5 hours. The sheet was removed, wiped free of nicotine, washed with water and dried. An individual placed the nicotine impregnated sheet between his gums and cheek and reported a prolonged sensation of enjoyment and nicotine stimulation due to the slowly released nicotine.

When the above procedure was carried out with a polypropylene sheet in place of the polyethylene sheet, similar results were reported upon testing.

EXAMPLE 12

Pouch Design Oral Nicotine Dispenser

Polyethylene strips with a size of about 1/16 inches by 1½ inches and a 0.005 inch thickness and impregnated with nicotine by soaking in nicotine at 125° F. for 1 hour. The strips and a polyethylene film were placed in a porous bag of material from a Lipton (Thomas S. Lipton, Inc., Englewood Cliffs, N.J. 07632 Flow Through tea bag and of a ½ inch × 1 inch size. The edges of the bag were heat-sealed with the film and strips therein.

An individual held the bag oral nicotine dispenser between his gums and cheek and reported a prolonged sensation of nicotine stimulation.

Changes may be made in particular components, steps and arrangements without departing from the scope of the invention as described by the following claims.

What is claimed is:

1. An oral nicotine dispenser comprising: nicotine and a water insoluble polymeric substance formed of numerous strips sorptively containing the nicotine and slowly releasing nicotine when said oral nicotine dispenser is in an oral environment.

2. An oral nicotine dispenser comprising: nicotine and a water insoluble polymeric substance formed of numerous strips contained in a porous bag, said dispenser sorptively containing the nicotine and slowly releasing nicotine when said oral nicotine dispenser is in an oral environment.

3. The oral nicotine dispenser of claim 2 wherein the porous bag consists essentially of a tea-bag fibrous sheet.

4. The oral nicotine dispenser of claim 2 wherein the porous bag has heat-sealed edges.

* * * * *